United States Patent [19]

Jarque et al.

[11] 4,173,705

[45] Nov. 6, 1979

[54] 2-(2-FUROYL)-4-METHYLPYRIDINE AND ITS METHYL IODIDE QUATERNARY SALT

[75] Inventors: Ricardo G. Jarque; Juan B. Cartes; Rosa L. Jimenez, all of Barcelona; Cristobal M. Roldan; Fernando R. Peinado, both of Madrid, all of Spain

[73] Assignee: Laboratorios Made, S.A., Madrid, Spain

[21] Appl. No.: 949,021

[22] Filed: Oct. 6, 1978

[30] Foreign Application Priority Data

Oct. 7, 1977 [ES] Spain ..................................... 462.990

[51] Int. Cl.$^2$ ........................................... C07D 405/02
[52] U.S. Cl. ..................................... 546/283; 424/263
[58] Field of Search ........................................ 546/283

[56] References Cited

PUBLICATIONS

Klingsberg, Pyridine and Its Derivatives, Part Two, pp. 2 to 6, 171 to 172, Interscience Publishers, Inc. NY (1961).

Riberau et al., C.R. Acad. Sc., Series C, vol. 280, pp. 293 to 296 (1975).

Berg et al., Chem. Abstracts vol. 72, Abst. No. 55273h (Abst. of So. Afr. 68 00,346) (1970).

Zelinski et al., J. Am. Chem. Soc., vol. 73, pp. 696 to 697 (1951).

Klingsberg, Pyridine and Its Derivatives, Part Four, pp. 152–154 and 217, Interscience Publishers, NY (1964).

*Primary Examiner*—John D. Randolph
*Attorney, Agent, or Firm*—Haseltine, Lake & Waters

[57] ABSTRACT

2-Cyano-4-methylpyridine is reacted in an inert atmosphere with an ethereal solution of freshly prepared 2-furoyl-lithium followed by acid hydrolysis to form 2-(2-furoyl)-4-methylpyridine which is then reacted with methyl iodide to form 2-(2-furoyl)-1,4-dimethylpyridinium iodide. Both furoyl compounds exhibit thermal and chemical analgesic properties.

6 Claims, No Drawings

2-(2-FUROYL)-4-METHYLPYRIDINE AND ITS METHYL IODIDE QUATERNARY SALT

The present invention relates to the preparation of 2-(2-furoyl)-1,4-dimethylpyridinium iodide of formula I and to that of an intermediate compound for its preparation, 2-(2-furoyl)-4-methylpyridine of formula II. The aforementioned compounds are new substances of possible pharmacological interest as analgesics and are prepared, according to the method of the invention, by the following reaction sequence.

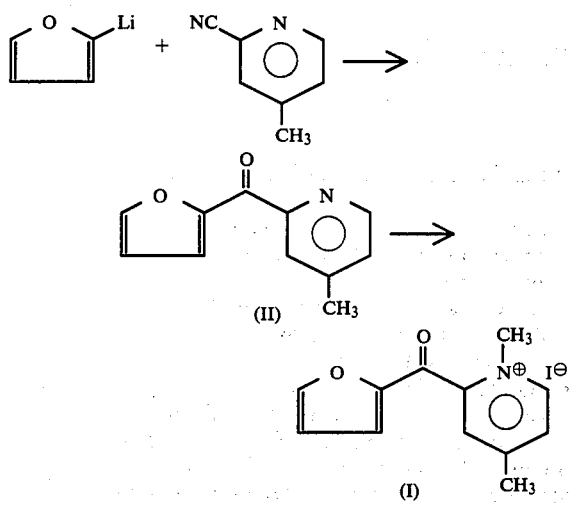

In the first part of the process 2-cyano-4-methylpyridine is reacted with freshly prepared 2-furyl-lithium by the action of butyl-lithium on furan. The reaction is carried out by adding, under an inert atmosphere, 2-cyano-4-methylpyridine dissolved in an anhydrous solvent to an ethereal solution of 2-furyl-lithium. After hydrolyzing the resulting mixture with hydrochloric acid and rendering it alkaline with sodium hydroxide, it is extracted with an organic solvent, thus obtaining 2-(2-furoyl)-4-methylpyridine (II). In a second stage of the process the thus prepared ketone II is converted into 2-(2-furoyl)-1,4-dimethylpyridinium iodide (I) by heating with a methyl halide, for example methyl iodide, in an anhydrous solvent, for example acetone.

The following examples are given by way of illustration only and in no way are they to be considered as limiting the scope of the invention.

EXAMPLE 1—Preparation of 2-(2-furoyl)-4-methylpyridine (II)

75 gr of freshly distilled furan dissolved in 180 ml of anhydrous ether are placed in a four-liter reactor and 800 ml of a 1,3 N ethereal solution of freshly prepared butyl-lithium are slowly added under a nitrogen atmosphere, keeping the temperature at $-20°$ C. The reaction mixture is then allowed to reach room temperature, following which it is boiled to reflux for seven hours. It is then cooled to $-20°$ C. and 116 gr of 2-cyano-4-methylpyridine dissolved in one liter of anhydrous benzene are added drop by drop. Upon completion of the addition, the mixture is boiled to reflux for two and a half hours, following which it is cooled and 6 N hydrochloric acid is carefully added until an acid pH is reached. The organic layer is removed by decanting, said layer is washed with 6 N hydrochloric acid, the aqueous layers are collected, the residual ether is removed by distilling and once 100° C. are reached the mixture is boiled to reflux for one and a half hours. Following this, the reactor is cooled externally, 50% sodium hydroxide is added until a basic pH is reached and the resulting solution is extracted with chloroform. After being dried once over anhydrous magnesium sulphate and evaporated to dryness, the organic layer is purified by chromatography on silica gel in a continuous flow column using benzene as eluent, providing 93 gr of 2-(2-furoyl)-4-methylpyridine (II) (Yield 51%). An analytical sample recrystallized from ether has a melting point of 111-2° C. Analysis calculated for $C_{11}H_9NO_2$: C: 70.58; H: 4.81; N: 7.48. Found: C: 70.48; H: 5.11; N: 7.20.

EXAMPLE 2—Preparation of 2-(2-furoyl)-1,4-dimethylpyridinium iodide (I)

49.7 gr of methyl iodide dissolved in 43 ml of anhydrous toluene are added to a solution of 5.5 gr of 2-(2-furoyl)-4-methylpyridine in 35.5 ml of anhydrous acetone. The mixture is kept under reflux for ninety-six hours. Following this, it is cooled for twelve hours. 8.1 g (Yield: 84%) of 2-(2-furoyl)-1,4-dimethylpyridinium iodide (I) with a melting point of 190°–95° C. are removed by filtering. An analytical sample recrystallized from ethanol has a melting point of 202-3° C. Analysis calculated for $C_{12}H_{12}NO_2I$: C: 43.78; H: 3.67; N: 4.25. Found: 43.76; H: 3.73; N: 4.50.

PHARMACOLOGICAL PROPERTIES OF THE PRODUCTS OF THE INVENTION

Products (I) 2-(2-furoyl)-1,4-dimethylpyridinium iodide (II) 2-(2-furoyl)-4-methylpyridine They are products with analgesic activity. Their toxicity and activity have been compared with dextropropoxyphene.

A—ACUTE TOXICITY

Acute toxicity studies were performed on I.C.R. Swiss albino mice, of both sexes, weighing $30\pm2$ g, kept fasting for 24 hours prior to the experiment. The room temperature and relative humidity were kept constant. The products were administered intraperitoneally, counting the number of deaths 48 hours after the treatment. The calculation of the lethal dose 50 ($LD_{50}$) was made by the Litchfield-Wilcoxon test. The results obtained were:

TABLE I

| Products | $LD_{50}$ (mg/kg) |
|---|---|
| I | 75 |
| II | 130 |
| Dextropropoxyphene | 140 |

B—ANALGESIC ACTIVITY

1—Thermal analgesia

The thermal analgesic effect was studied on I.C.R. Swiss albino mice. The hot plate technique was used at 55° C. Batches of 10 mice were used.

The products under study were administered intraperitoneally and after 30 minutes the mice were placed on the hot plate, counting the number of seconds they took to jump. Batches of control animals which are only injected with distilled water are used.

The results are given in tables 2 and 3.

TABLE II

| Treatments | Dose mg/kg | Jumping Time in sec. $\bar{x} \pm$ S.E.M.(1) | Significance of differences Controls | Dextropropoxyphene |
|---|---|---|---|---|
| Control | — | 22 ± 7.3 | — | — |
| I | 30 | 62.2 ± 7.76 | p∠0.0002 | N.S. |
| Dextropropoxyphene | 30 | 51 ± 8.4 | p∠0.005 | — |

(1)Mean values ± standard error of the mean.

Product I has thermal analgesic activity of the same intensity as dextropropoxyphene.

TABLE III

| Treatments | Dose mg/kg | Jumping Time in sec. $\bar{x} \pm$ S.E.M.(1) | Significance of differences Controls | Dextropropoxyphene |
|---|---|---|---|---|
| Control | — | 22 ± 7.3 | — | — |
| II | 30 | 55.9 ± 7.4 | p∠0.001 | N.S. |
| Dextropropoxyphene | 30 | 51 ± 8.4 | p∠0.005 | — |

Product II has thermal analgesic activity of the same intensity as dextropropoxyphene.

2—Chemical analgesia

The analgesic effect was studied on I.C.R. Swiss albino mice with the acetic acid writhing technique. Batches of 10 mice were used.

The products under study were administered intraperitoneally and after 30 minutes 0.25 ml of 1% acetic acid was injected intraperitoneally. A batch of control animals which only received acetic acid was used. The number of writhes in each mouse was counted 20 minutes after administration of the acetic acid. The results are given in tables IV and V.

TABLE IV

| Treatments | Dose mg/kg | No. of writhes $\bar{x} \pm$ S.E.M.(1) | Significance of differences Controls | Dextropropoxyphene |
|---|---|---|---|---|
| Control | — | 115.5 ± 11.6 | — | — |
| I | 25 | 55.6 ± 6.58 | p∠0.0005 | N.S. |
| Dextropropoxyphene | 25 | 54.7 ± 8.6 | p∠0.001 | — |

Product I has chemical analgesic activity of the same intensity as dextropropoxyphene.

TABLE V

| Treatments | Dose mg/kg | No. of writhes $\bar{x} \pm$ S.E.M.(1) | Significance of differences Controls | Dextropropoxyphene |
|---|---|---|---|---|
| Control | — | 101.5 ± 7.3 | — | — |
| II | 25 | 53.2 ± 2.6 | p∠0.00005 | p∠0.00005 |
| Dextropropoxyphene | 25 | 76.8 ± 3.1 | p∠0.01 | — |

Product II has chemical analgesic activity which is significantly greater than that of dextropropoxyphene.

We claim:
1. 2-(2-Furoyl)-1,4-dimethylpyridinium iodide.
2. 2-(2-Furoyl)-4-methylpyridine.
3. A process for preparing 2-(2-furoyl)-1,4-dimethylpyridinium iodide comprising the steps of reacting 2-cyano-4-methylpyridine under a nitrogen atmosphere with an ethereal solution of freshly prepared 2-furyllithium, hydrolyzing the reaction mixture under acid conditions to form 2-(2-furoyl)-4-methylpyridine, and heating the 2-(2-furoyl)-4-methylpyridine in the presence of methyl iodide to form 2-(2-furoyl)-1,4-dimethylpyridinium iodide.
4. A process for preparing 2-(2-furoyl)-4-methylpyridine comprising reaction 2-cyano-4-methylpyridine with freshly prepared 2-furyl-lithium under an inert atmosphere.
5. The process of claim 4 wherein the 2-cyano-4-methylpyridine is added to the 2-furyl-lithium at about −20° C., the reaction mixture is refluxed to complete the reaction and then hydrolyzed in hydrochloric acid.
6. The process of claim 5 wherein the hydrolysis product is made alkaline, extracted with chloroform, and purified by chromatography on silica gel.

* * * * *